US009291616B2

(12) United States Patent
Vyas et al.

(10) Patent No.: US 9,291,616 B2
(45) Date of Patent: Mar. 22, 2016

(54) FUNGAL-DERIVED CARBOHYDRATE-CONJUGATED SCAFFOLD

(75) Inventors: Jatin M. Vyas, Milton, MA (US); Jenny M. Tam, Brookline, MA (US); Michael K. Mansour, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 14/110,443

(22) PCT Filed: Apr. 9, 2012

(86) PCT No.: PCT/US2012/032695
§ 371 (c)(1),
(2), (4) Date: Dec. 23, 2013

(87) PCT Pub. No.: WO2012/139089
PCT Pub. Date: Oct. 11, 2012

(65) Prior Publication Data
US 2014/0127267 A1 May 8, 2014

Related U.S. Application Data

(60) Provisional application No. 61/473,541, filed on Apr. 8, 2011, provisional application No. 61/547,335, filed on Oct. 14, 2011.

(51) Int. Cl.
*C12Q 1/00* (2006.01)
*G01N 33/569* (2006.01)
*G01N 33/50* (2006.01)
*A61K 47/48* (2006.01)
*A61K 39/00* (2006.01)

(52) U.S. Cl.
CPC ........ *G01N 33/5091* (2013.01); *A61K 39/0002* (2013.01); *A61K 47/48892* (2013.01); *G01N 33/56961* (2013.01)

(58) Field of Classification Search
CPC ................................................ G01N 33/5091
See application file for complete search history.

(56) References Cited

U.S. PATENT DOCUMENTS

| 7,722,857 B2 | 5/2010 | Ohno et al. |
| 2004/0127458 A1 | 7/2004 | Hunter et al. |
| 2011/0177532 A1 | 7/2011 | Rubin-Bejerano et al. |

FOREIGN PATENT DOCUMENTS

| WO | 2008/057501 | 5/2008 |
| WO | 2009/134891 | 11/2009 |

OTHER PUBLICATIONS

Ishibashi et al., International Immunopharmacology, 2(8):1109-22 (2002) "Relationship between the physical properties of Candida albicans cell well beta-glucan and activation of leukocytes in vitro".
Dykstra et al., Innate Immunity 17(4):388-7402 (2010) "Defined particle ligands trigger specific defense mechanisms of macrophages".
Goodridge et al. "Detection of fungal particles by Dectin-1 triggers reorganization of macrophage membrane proteins to form a "phagocytic cynapse"" The Journal of Immunology 182:134.35 (2009) Abstract.
Gao "Cytokine stimulating (in vitro) effect on human monocytes of conjugates of soluble curdlan and albumin microbeads" Drug Delivery 4(4):239-245 (1997).
Supplementary European Search Report from corresponding European Patent Application No. EP12757430 mailed Nov. 24, 2014.
Ishibashi et al., International Immunopharmacology, 2(8)1109-22 (2002). "Relationship between the physical properties of Candida albicans cell well beta-glucan and activation of leukocytes in vitro." Abstract only.
Manfredi et al., Arch Intern Med, 157:64-69 (1997). "Fluconazole as prophylaxis against fungal infection in patients with advanced HIV infection."
Palma et al., The Journal of Biological Chemistry, 281(9):5771-79 (2006). "Ligands for the beta-glucan receptor, dectin-1, assigned using 'designer' microarrays of oligosaccharide probes (neoglycolipids) generated from glucan polysaccharides."
Pasqualotto et al., Business Briefing: European Oncology Review, 1-11 (2005). "Diagnosis of invasive fungal infections—current limitations of classical and new diagnostic methods."
Pickering et al., Journal of Clinical Microbiology, 43(12):5957-62 (2005). "Evaluation of a (1-3)-beta-d-glucan assay for diagnosis of invasive fungal infections."
Rubin-Bejerano et al., Cell Host Microbe, 2(1):55-67 (2007). "Phagocytosis by human neutrophils is stimulated by a unique fungal cell wall component."
Sklar et al., Annual Review of Biophysics and Biomolecular Structure, 31:97-119 (2002). "Flow cyotmetric analysis of ligand-receptor interactions and molecular assemblies."
Aouadi et al., "Orally delivered siRNA targeting macrophage Map4k4 supresses systemic inflammation." Nature, 458:1180-1184 (2009).
Chan et al., "The effects of beta-glucan on human immune and cancer cells" Journal of Hematology & Oncology, 2(25):1-11 (2009).
Hong et al., "Mechanism by which orally administered beta-1,3-glucans enhance the tumoricidal activity of antitumor monoclonal antibodies in murine tumor models." The Journal of Immunology, 173:797-806 (2004).
Karagiannis et al., "Minicells overcome tumor drug-resistance." Nature Biotechnology, 27(7):620-621 (2009).
Vetvicka, Glucan-immunostimulant, adjuvant, potential drug, World Journal of Clinical Oncology, 2(2):115-119 (2011).

*Primary Examiner* — Albert Navarro
(74) *Attorney, Agent, or Firm* — Nixon Peabody LLP

(57) ABSTRACT

The present invention provides for compositions and methods for a purified fungal carbohydrate-linked polymer bead platform, which can serve as an artificial fungus-like particle to measure specific patient immune responses to fungal carbohydrate antigens. A specific embodiment comprises a purified β-1,3-glucan chemically conjugated to a polymer bead.

18 Claims, 7 Drawing Sheets

FUNGAL-DERIVED CARBOHYDRATE-CONJUGATED SCAFFOLD

CROSS REFERENCE TO RELATED APPLICATIONS

This application is a 35 U.S.C. §371 National Phase Entry Application of International Application No. PCT/US2012/032695 filed Apr. 9, 2012, which designates the U.S., and which claims benefit under 35 U.S.C. §119(e) of U.S. Provisional Application No. 61/473,541 filed Apr. 8, 2011, and U.S. Provisional Application No. 61/547,335 filed Oct. 14, 2011, the contents of each of which are incorporated fully herein by reference in their entireties.

FEDERAL FUNDING

The present invention was made with government support under grants No. 1R01AI092084-01A1 and No. T32AI007061-35, awarded by the National Institutes of Health. The U.S. government has certain rights in the invention.

FIELD

The present invention relates to molecular immunology, biology, and medicine. Embodiments provide for compositions and methods for a fungal carbohydrate-linked bead system; and use of fungal like particles, for example, to identify immunodeficiency.

BACKGROUND

Life-threatening fungal infections continue to rise primarily due to a growing immunocompromised patient population. These patients include people receiving chemotherapy as well as ones with autoimmune inflammatory diseases undergoing immunomodulating treatments such as TNF-α blockade (e.g., for treating Crohn's disease, rheumatoid arthritis, or lupus erythematosus). Moreover, there has been an unprecedented increase in the number of fungal infections as the use of biologics and chemotherapeutic agents has increased. Such fungal infections are associated with a high mortality.

A major barrier to delivering appropriate clinical care to the immunocompromised population has been inability to predict which of these subjects will develop invasive fungal infections. The dramatic rise in use of the serum β-D-glucan and galactomannan assays evidences the desperate need for these diagnostics. These tests are neither sufficiently sensitive nor specific, however, for the diagnosis of invasive fungal infection. Hence, there remains a need for a diagnostic tool that identifies those individuals with deficits in fungal immunity, that will allow clinicians to focus on delivering specific therapeutics and prophylactic counter-measures. There also remains a need for a fungal immunogen that may raise at least some level of protective response against fungal infection.

SUMMARY

The present invention provides for compositions and methods for a purified fungal carbohydrate-linked polymer bead platform, which can serve as an artificial fungus-like particle to measure specific patient immune responses to fungal carbohydrate antigens. Coupling different carbohydrate antigens to polymer scaffolds (e.g., beads) allows clinicians to probe the immunity to specific fungal infections. For example, glucan-specific responses may signify immunity to *Aspergillus* and *Candida* species, but mannan-specific immune responses are essential only for *Candida* species. The present fungal carbohydrate antigen platform allows characterization of specific immunity on an individual patient basis (i.e., personalized medicine). Identifying deficits in immunity to each of these species allows for the appropriate and necessary indications, including prophylactic antibiotics and vaccinations, required to treat each individual patient before or as they undergo immunomodulating treatments.

An embodiment of the present invention provides for a composition of matter comprised of synthetic and pathogen-derived carbohydrates conjugated by covalent bonds to a particle scaffold. The particle scaffold can comprise of a biocompatible polymer, such as polyethylene glycol, agars, or poly(lactic-co-glycolic acid) (PLGA). In a particular embodiment, the scaffold is an amino-terminated polystyrene microsphere. The carbohydrate can be fungal-specific, such as a glucan or mannan. In a specific embodiment, the carbohydrate is β-1,3-glucan. In a specific embodiment, the carbohydrate is mannan. Due to the stability and purity of the carbohydrate surface, the beads of this particular embodiment are useful for immunoprecipitation studies to purify receptors and other proteins associated with this fungal-derived carbohydrate.

Another embodiment of the invention provides for a composition of matter comprised of one or more pathogen-derived components conjugated by covalent bonds to a particle scaffold. The scaffold can be comprised of a biocompatible polymer. The pathogen-derived component can comprise a component of the cell wall, such as a carbohydrate. The component of the cell wall can comprise one or more carbohydrates. For example, a cell wall carbohydrate can be a fungus-specific carbohydrate such as a glucan or mannan. In a particular embodiment, the carbohydrate is β-1,3-glucan. In another specific embodiment, the carbohydrate is mannan.

In some embodiments, the fungal carbohydrate-linked polymer bead platform of the present invention has a shape designed to mimic the geometry of the synthetic carbohydrate or the pathogen.

Other embodiments of the present invention provide for the use of fungal-like particles to identify immunodeficiency. More specifically, for example, the technology presented herein creates a monodisperse population of artificial pathogens that replicate the size and geometry of pathogenic yeast. By covalently attaching purified β-1,3-glucan, a major cell wall component of fungal pathogens (such as *Candida albicans* and *Aspergillus funligatus*) to the surface of polystyrene beads, users can directly probe pathways related to Dectin-1, the major receptor for β-1,3-glucan. As opposed to the use of live organisms or cell wall fragments, which are complex in composition and contain multiple cell wall carbohydrate and protein components, and thereby generate non-Dectin-1 responses, the present "artificial pathogens" provide a method to directly probe the immune response to β-1,3-glucan.

Hence, another embodiment of the present invention provides for a method to determine whether a population of cells is immunocompromised for fungal infection by obtaining a population of peripheral blood mononuclear cells (PBMCs), or particularly macrophages; contacting the PBMCs with the β-1,3-glucan beads of the present invention; detecting a cytokine response (e.g., a TNF-α or IL-6 response) compared with a known baseline response. The contacting may be for a period of about 8 to about 24 hours, inclusive. The detecting of the cytokine response can comprise an ELISA, for example a TNF-α ELISA. The baseline response can be the level of cytokine (e.g., TNF-α or IL-6) stimulated in a healthy, non-immunocompromised cell population. The population of peripheral blood mononuclear cells (PBMCs), bone marrow cells, or macrophages can be obtained from a subject, such as a human subject.

Alternatively, another embodiment of the present invention provides for a method to determine whether a population of cells is immunocompromised for fungal infection because it lacks sufficient Dectin-1 on the cells surfaces, by obtaining a population of PBMCs, bone marrow cells, or particularly macrophages; contacting the cells with β-1,3-glucan-conjugated beads; observing the binding of the beads to the Dectin-1 on the PBMC cells (e.g., by microscopy); and comparing the binding with that of a baseline level. The β-1,3-glucan beads can be labeled with a detectable label such that the binding of the beads to the PBMCs comprises confocal fluorescence microscopy or FACS.

In some embodiments, the invention provides kits that include the artificial fungus-like particle. In particular, the artificial fungus-like particle is suitable for a diagnostic assay kit, which diagnostic assay can be an automated assay.

DETAILED DESCRIPTION

Figure 1:
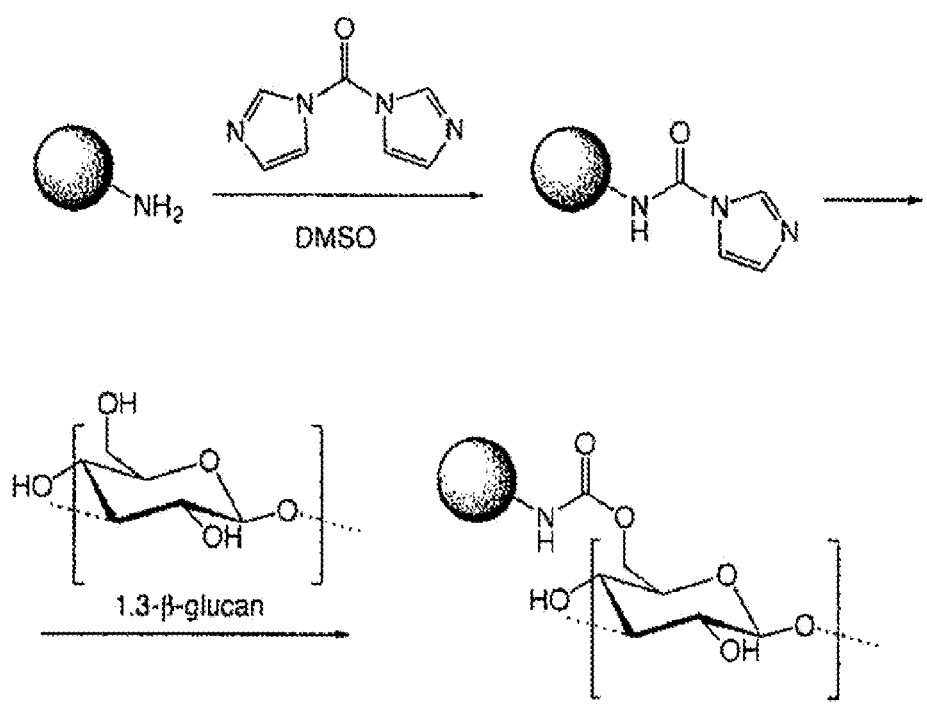
FIG. 1 is a schematic overview of β-1,3-glucan conjugation, showing the expected major product (linkage through 1° hydroxyl on 6 position of saccharide). Amine-terminated microspheres were incubated in a solution of 0.5 M 1,1'-carbonyldiimidazole in DMSO for 1 hour at room temperature. After washing, beads are added and shaken in a solution β-1,3-glucan derived from *Saccharomyces cerevisiae* dissolved in DMSO. β-1,3-glucan forms a linkage through the primary hydroxyl on the 6th position of the saccharide. Color versions of some of the Figures are available at Tam et al., *Use of Fungal Derived Polysaccharide-Conjugated Particles to Probe Dectin-1 Responses in Innate Immunity*, 4 Integrative Biol. 220 (2012).

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The number of life-threatening fungal infections has risen in immunocompromised patients, and identification of the rules that govern an appropriate immune response is essential to develop better diagnostics and targeted therapeutics. The outer cell wall component on many pathogenic fungi includes the carbohydrates β-1,3-glucan and β-1,6-glucan. Dectin-1, a pattern recognition receptor present on the cell surface of innate immune cells, binds specifically to β-1,3-glucan and β-1,6-glucan. Previously, the presence of multiple types of carbohydrate moieties on fungal cell walls has presented a barrier in understanding the exact immunological response to pathogen-derived carbohydrate epitopes.

Briefly, the present invention provides for a system of "fungal like particles" that consisted of polymer (e.g., polystyrene) beads that mimic the three-dimensional shape of the fungal cell, coated covalently with purified fungal polysaccharide (e.g., purified β-1,3-glucan or mannan derived from *Saccharomyces cerevisiae*). For example, the size of the particle can be selected from 2 μm to 3.4 μm, inclusive (see Reponen, 22 Aerosol Sci. Technol. 11 (1995)), or about 3 μm±35%. In a particular embodiment, the polymer particle is a 3 μm±1% polystyrene bead.

The morphology of the β-1,3-glucan layer was examined by immunofluorescence, flow cytometry, and immuno-transmission electron microscopy. The covalent linkages of the β-1,3-glucan to the bead surface were stable after subjecting the beads to detergents. By pre-treating β-1,3-glucan beads with laminarinase, a specific β-1,3-gluconase, the reactivity of the anti-β-1,3-glucan antibody was abrogated in comparison to treatment with proteinase K, indicating that the coating of these beads was predominantly β-1,3-glucan. A TNF-α response to the artificial fungus-like particle was measured by stimulating bone-marrow derived macrophages with the β-1,3-glucan-coated beads, and showed a dose dependent response as compared with soluble β-glucan, insoluble β-1,3-glucan, uncoated beads, and soluble β-1,3-glucan mixed with uncoated beads. Additionally, β-1,3-glucan beads were incubated with GFP-Dectin-1-expressing macrophages and imaged using confocal microscopy. The β-1,3-glucan-beads were taken up within minutes and retained Dectin-1 recruitment to the phagosome. The present invention describes a unique fungal-like particle system that permits immunologists to probe the critical steps in early recognition of pathogen-derived fungal carbohydrate antigens by innate immune cells.

Invasive fungal infections, such as candidiasis, have become a leading cause of death among immunocompromised patients, e.g., leukemic patients, cancer patients with neutropenia, and recipients of immunomodulatory agents including TNF-α blockers. Romani, 4 Nat. Rev. Immunol. 1 (2004). In the intensive care unit, candidal infections have become the third-most-common bloodstream infection after *Staphylococcus aureus* and *Pseudomonas aeruginosa*, and has a crude mortality rate of 30% to 40%. Arendrup, 16 Curr. Op. Crit. Care 445 (2010). The high incidences of infection and mortality highlight the need for better diagnostics and improved antifungal therapies. To improve outcomes for patients with invasive fungal infections, knowledge of the key molecular pathways within relevant immune cells, including a detailed understanding of the dynamic host-pathogen interactions upon phagocytosis, is vital in order to generate strategies to augment the host response.

Anti-fungal immunity is complex, and involves both innate and adaptive immunity. Early innate defenses include phagocytes, such as macrophages, neutrophils and dendritic cells, which recognize, ingest, and degrade the invading pathogen. Pattern-recognition receptors (PRRs) recognize highly conserved microbial epitopes known as pathogen-associated molecular patterns (PAMPs). The Toll-like receptors (TLRs) are the best-studied family of PRRs. TLRs can provide strong activating signals to professional antigen presenting cells through activation of the NF-κB pathway. Medzhitov, 449 Nat. 819 (2007). Another PRR on the cell surface is Dectin-1, a type H membrane protein and C-type lectin that is highly expressed on phagocytes. Brown, Nat. Rev. Immunol. (2006). Dectin-1 recognizes the carbohydrate epitope β-1,3-glucan, which is a major PAMP and constitutes the major cell wall component of fungi such as *Candida albicans, S. cerevisiae*, and *Aspergillus fumigatus*; although some β-1,6-linked side chains of varying length and distribution are also observed. Tsoni & Broan, 1143 Ann. N.Y. Acad. Sci. 45 (2008); Bowman & Free, 28 Bioessays 799 (2006); Riggi & Di Luzio 200 Am. J. Physiol. 297 (1961). Dectin-1 is required for proper modulation of immune responses, and reports have shown that patients with mutations in Dectin-1 are at higher risk for invasive fungal infections. Cunha et al., 116 Blood 5394 (2010); Ferwerda et al., 361 N. Engl. J. Med. 1760 (2009). The cytoplasmic tail of Dectin-1 contains an immunoreceptor tyrosine-based activation (ITAM)-like motif. Ariizunni et al., 275 J. Biol. Chem. 20157 (2000). Upon ligation of the extracellular domain of Dectin-1, the tyrosine residue within the cytoplasmic ITAM motif is phosphorylated. Herre et al., 104 Blood 4038 (2004). This phosphorylation event results in recruitment of spleen tyrosine kinase (Syk) and caspase recruitment domain protein 9 (Card9). Hara et al., 8 Nat. Immunol. 619 (2007). Ultimately, this pathway leads to the activation of NF-κB, and production of reactive oxygen species as well as pro-inflammatory cytokines including TNF-α and IL-12. Hernanz-Falcón et al., 39 Eur. J. Immunol. 507 (2009).

Isolated β-1,3-glucans can trigger immune responses, and there has been significant interest in their development as adjuvants and as immunotherapeutic agents. Pietralla et al., 28 Vaccine 1717 (2010). The ability of β-1,3-glucans to modulate immunity is influenced by their polymer length, degree of branching, and tertiary structure. Bohn & BeMiller, 28 Carbo. Pol. 3 (1995). Although not yet fully understood, these attributes can influence the interaction of carbohydrate antigens with their cognate receptors, particularly Dectin-1. Adams et al., 325 J. Pharmacol. Exp. Therap. 115 (2008). Both soluble and insoluble β-1,3-glucan polymers have been shown to bind to Dectin-1, although only insoluble β-1,3-glucan activates Dectin-1 signaling to produce cytokine responses. Goodridge et al., 472 Nat. 471 (2011). Zymosan, a derivative of the *S. cerevisiae* cell wall, has been used as a model substrate to define the immune response to fungal cell walls. Brown et al., 401 Nat. 811 (1999). Zymosan particles are heterogeneously sized and composed of a complex mixture of polysaccharides and proteins whose exact composition is unknown.

The Dectin-1 response to β-1,3-glucan antigens is characterized herein by construction of an "artificial fungal pathogen." A particular embodiment of this fungus-like particle comprises a purified β-1,3-glucan (isolated from *S. cerevisiae*) covalently conjugated to a polystyrene bead platform. This platform allows direct probing of the Dectin-1 response to a pure β-1,3-glucan fraction, as opposed to the use of live organisms or cell wall particulates, which are complex in composition and contain multiple cell wall carbohydrate and protein components, all of which can generate non-Dectin-1-specific responses. The use of inert polymer beads (e.g., polystyrene) as a scaffold also replicates the size and geometry of the pathogenic yeast without the additional contribution of secreted products by the pathogen (Champion & Mitragotri, 103 PNAS 4930 (2006)), in addition to creating a monodisperse population to probe the immune response. A common approach cited in the literature is the use of physically adsorbed β-1,3-glucan to a polymeric bead surface (Goodridge et al., 2011; Wheeler & Fink, 2 PLoS Pathog. e35 (2006)), but this approach failed to provide stability of the glucan layer on the bead surface, especially in the harsh degradative environments found in the endocytic pathway after phagocytosis. Because this pathway is important in characterizing immunocompetent activity, for example the phagocytosis activity of macrophages in response to particular pathogens, there was a need for an alternative approach.

Additionally, carbohydrates, including purified dextran, soluble β-1,3-glucan, and other synthetic polysaccharides have been immobilized using diverse chemical strategies including photochemical immobilization (Wang et al., 22 Bioconj. Chem. 26 (2011)), reductive animation (Konopski et al., 33 Scand. J. Immunol. 297 (1991)), EDC conjugation using carboxylate modified sugars (Song et al., 132 J. Am. Chem. Soc. 11428 (2010)), and utilizing divinyl sulfone (DVS)-modified surfaces (Cheng et al., 22 Bioconj. Chem. 50 (2011)). These approaches require considerable synthetic chemistry expertise, either to install specific chemical functions on the carbohydrate of interest, or to construct the desired polysaccharide, or both.

To probe the immune response to artificial fungal pathogens, e.g., β-1,3-glucan binding to Dectin-1, the present invention employs a simple method to attach purified carbohydrates from biologically relevant fungi to polymeric beads using minimal steps. The chemistry is based on activation of amine-functionalized beads with 1,1-carbonyldiimidazole (CDI) and addition of purified carbohydrates, such as β-1,3-glucan or mannan, to create a surface which mimics the yeast cell wall. These particles, which resemble pathogenic yeast in size and surface chemistry, are referred to herein as "artificial fungal pathogens" or "fungus-like particles" and the like.

The present artificial fungal pathogens were characterized using differential interference contrast (DIC) microscopy, immunofluorescence, and transmission-electron microscopy (TEM). The covalent interaction of the β-1,3-glucan layer to the surface of the bead was confirmed by a series of increasingly stringent detergent so treatments. Purity of the β-1,3-glucan layer was also determined by incubating the beads with laminarinase, a specific β-1,3-gluconase. The amount of TNF-α or IL-6 produced by stimulating bone marrow derived macrophages was also measured by ELISA, and showed a dose dependent response when compared with soluble β-1,3-glucan, uncoated beads, and soluble β-1,3-glucan mixed with uncoated beads. Dectin-1 response was investigated by observing direct phagocytosis of β-glucan coated artificial pathogens by live RAW macrophages expressing a GFP-Dectin-1 fusion protein using spinning disk confocal microscopy. Macrophage phagocytosis was also observed in response to mannan-coated particles. By providing the present platform to probe directly immune responses to the purified carbohydrate, e.g., β-1,3-glucan or mannan, presented in the context of the artificial fungal pathogen, immunologists can dissect the critical steps in the early recognition of pathogen-derived fungal carbohydrate antigens in innate immunity. Additionally, this system permits the addition of other relevant pathogen-derived carbohydrates to polymeric beads to analyze the specific contribution of these ligands in the immune response.

More specifically, purified β-1,3-glucan carbohydrates were covalently conjugated to polystyrene beads. 1,1'-Carbonyldiimidazole (CDI) was used to conjugate amine-terminated polystyrene beads by activating the amino groups on the bead surface (FIG. 1). The resulting imidazole carbamate intermediates are sufficiently reactive to acylate primary and secondary hydroxyl groups without the use of strong bases. CDI has previously been used to conjugate hydroxyl-containing small molecules onto agarose beads, and the resulting carbamate linkage formed between the hydroxyl groups and the bead surface is noncharged and highly stable under immunoprecipitation conditions. Wang et al., 19 Bioconj. Chem. 585 (2008). Therefore, this strategy was used to conjugate β-1,3-glucan to amino-terminated microspheres. Following CDI activation, a DMSO solution of β-1,3-glucan was incubated with the beads to complete the coupling. Alternatively, mannan was conjugated to the surface of polystyrene beads using this chemistry. Alternative conjugation reagents are known in the art, see, e.g., Hermanson, BIOCONJUGATE TECHNIQUES (Acad. Press, 1996); U.S. Patent Pub. No. 2011/0177532.

Preparations of β-1,3-glucan that are insoluble in water elicit stronger innate immune responses than soluble preparations, likely due the higher valency of the insoluble material endowing an increased capacity to crosslink Dectin-1 at the cell surface. Goodridge, et al., 2011. Therefore, a β-1,3-glucan from *S. cerevisiae* that was soluble in DMSO was used. The use of DMSO has the additional advantage of minimizing any competing hydrolysis of surface imidazole carbamates during the reaction. Coupling of β-1,3-glucan is expected to proceed mostly through the primary hydroxyl groups of the polysaccharide chain, although a small fraction of coupling through the secondary hydroxyl groups is also expected. Wang et al., 2008. Similarly, mannan derived from *S. cerevisiae* was conjugated to polystyrene beads.

The ability to label β-1,3-glucan beads with NHS ester dye after carbohydrate conjugation strongly suggests that additional amine sites not activated by CDI are present on the bead surface. These sites would be available for conjugation with other dyes or with other biomolecules such as pathogen-derived proteins or peptides. By incorporating separate cell wall components to the polymer bead, distinct host responses to combinations of individual pathogen components could be ascertained.

Other cell wall components that may be used in the artificial fungus-like particle include, for example, β-1,6-glucan; β1,3-glucan having β-1,6-glucan branches; β-1,3-glucan laminarins; the glucuronoxylomannan, glucuronoxylomannan-peptide mimotopes, or other components of the polysaccharide capsule of *Cryptococcus neoformans*; agglutinin-like sequences, secreted aspartic proteinase2, 65 Da mannoprotein, or β-1,2-mannosides from *Candida*; antigen2 or β-1,3-glucosyl transferases of *Coccidiomycetes*; p55 glycoprotein or kexin protease of *Pneuocystis*; or 43 kDa protein of *Paracoccidoides*. The β-1,3-glucan, mannan, or other components can be derived from natural or recombinant organisms, or be chemically synthesized.

Figure 2A:
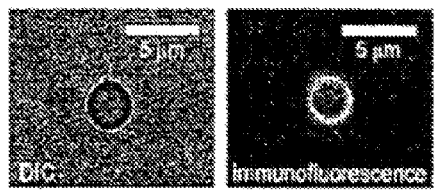
FIGS. 2A-2F show the surface characterization of β-1,3-glucan beads. (2A) Immunofluorescence using anti-β-1,3-glucan antibody comparing β-1,3-glucan conjugated beads with (2D) unconjugated beads under DIC and confocal microscopy. (2B, 2E) Flow cytometry comparing (2B) β-1,3-glucan is beads compared with (2E) unconjugated beads incubated with anti-β-1,3-glucan antibody conjugated to Alexa floor 488. (2C, 2F) Immunotransmission electron micrographs of (2C) β-1,3-glucan beads to (2F) uncoated beads; anti-β-1,3-glucan antibody visualized with gold nanoparticles (arrows).
Figure 2B:
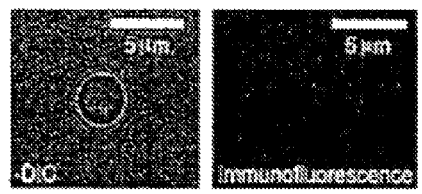

The present carbohydrate-linked beads characterized by immunofluorescence, flow cytometry, and transmission electron microscopy (TEM) showed uniform coating of β-1,3-glucan to the microsphere surface. More specifically, the carbohydrate layer on the coated beads was examined using differential interference contrast (DIC) microscopy to examine gross surface morphology of the beads and confocal immunofluorescent microscopy using an antibody against β-1,3-glucan (FIG. 2A-2E). By DIC, both the β-1,3-glucan coupled and uncoated beads show the same circular structure (FIGS. 2A, 2D). After incubation with anti-β-1,3-glucan antibody, the β-1,3-glucan-coated beads exhibited strong fluorescence, as compared with uncoated beads. To determine any non-specific binding, both bead types were also incubated with an isotype control antibody; neither bead type exhibited detectable fluorescence. Flow cytometry was also used to compare the distribution of carbohydrate on the labeled beads (FIGS. 2B, 2E). The beads coated in β-1,3-glucan show a sharp peak, indicating that the β-1,3-glucan beads were uniformly and densely coated specifically with the glucan (FIG. 2B). Incubation of the β-1,3-glucan-coated bead with the isotype control antibody showed little to no fluorescence signal. In contrast, the peak from the uncoated beads coated with the anti-β-1,3-glucan overlapped almost exactly to that of the isotype control antibody (FIG. 2E).

Figure 2C:
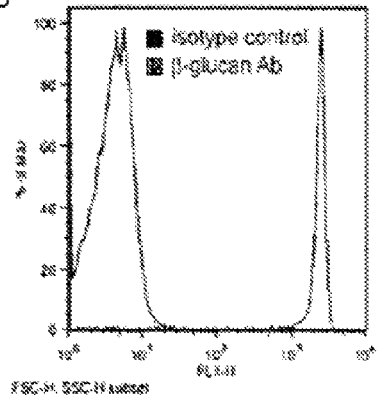
Figure 2D:
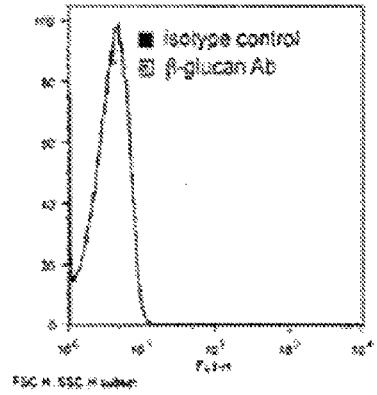
Figure 2E:
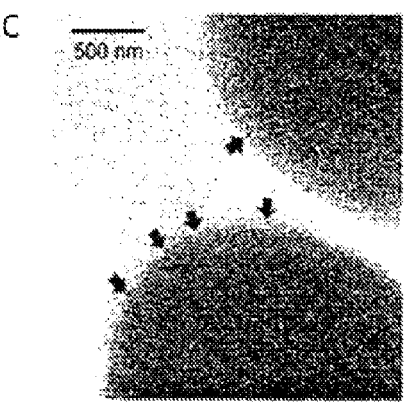
Figure 2F:
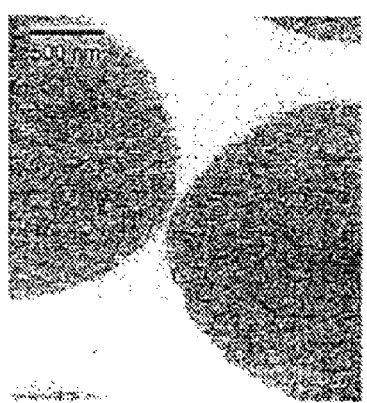

Immuno-TEM was also performed with the β-1,3-glucan beads to examine the surface of the beads as well as confirm additional antibody specificity to the β-1,3-glucan surface (FIGS. 2C, 2F). The surface of the β-glucan-coated beads shows a diffuse layer of electron density <50 nm in thickness not present on unmodified beads, which is likely indicative of the carbohydrate layer. The anti-β-1,3-glucan gold nanoparticles observed on the bead surface (FIG. 2C), show that this surface feature is specifically β-1,3-glucan. In contrast, the surface of the uncoated beads (FIG. 2F), show a smooth surface with no gold particles bound to the surface.

Figures 3A, 3B, 3C:
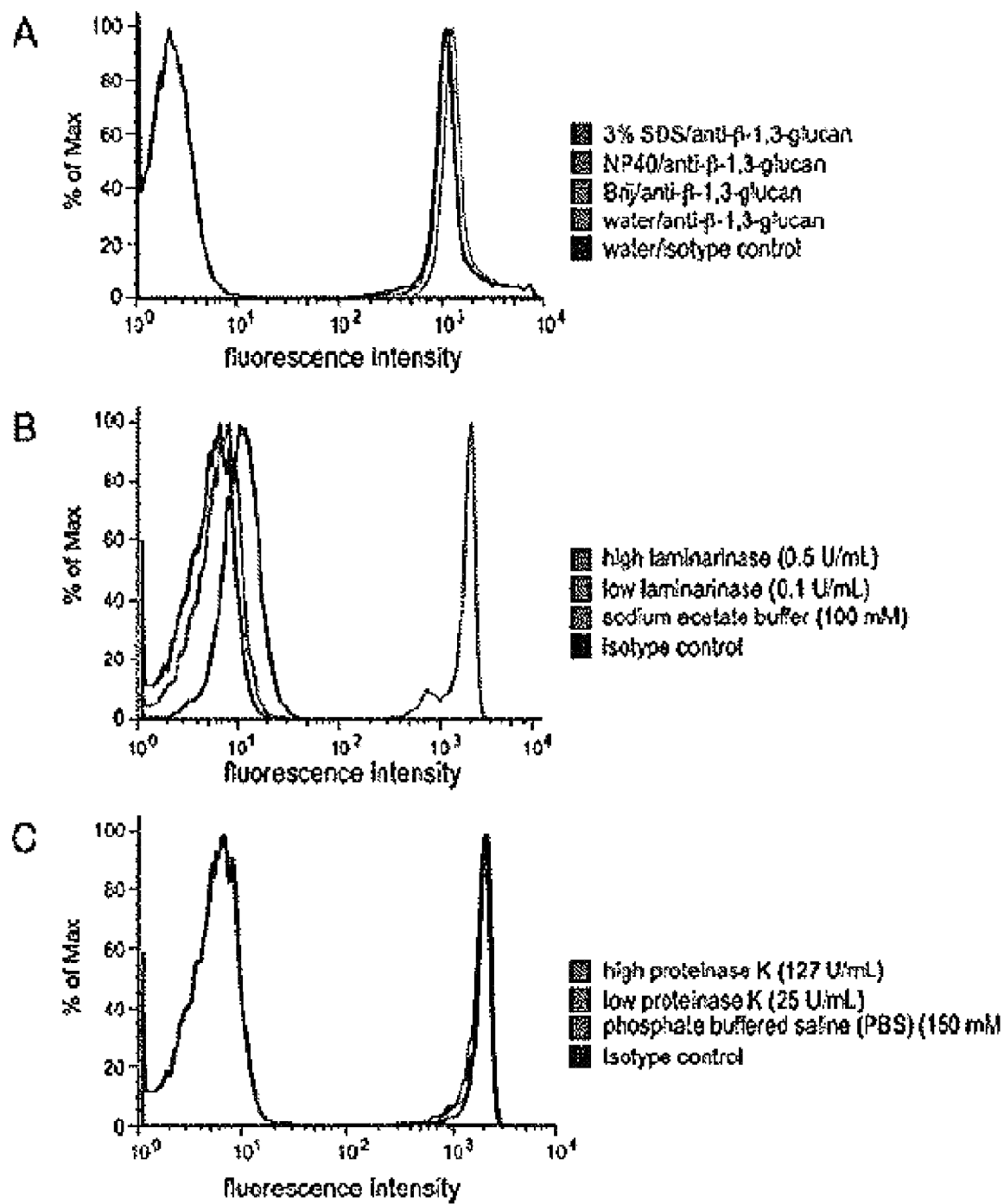
FIGS. 3A-3C show β-1,3-glucans conjugated to microspheres through covalent bonds. (3A) β-1,3-glucan beads were treated with increasingly stringent conditions for 1 hour. (3B) β-1,3-glucan beads were treated with laminarinase, a specific β-1,3-gluconase, as compared to (3C) proteinase K. In all conditions, surface β-1,3-glucan was detected using anti-β-1,3-glucan antibody.

Additionally, the β-1,3-glucan layer of this particular artificial fungal particle is stable with incubated with detergents. The stability of the carbamate linkage between the carbohydrate and the polystyrene beads was examined by subjecting the coupled β-1,3-glucan beads to detergents in concentrations typically used in immunoprecipitation: 3% SDS, 1% NP40, and 1% Brij 58, and analyzed by flow cytometry (FIG. 3A). After incubating the β-1,3-glucan coated beads with each detergent followed by rinsing, the beads were incubated with the β-1,3-glucan antibody, to determine the stability of the β-glucan coat, and assessed by flow cytometry. As a positive control, the β-1,3-glucan-coated beads were also incubated in PBS prior to antibody labeling. Surface staining of β-1,3-glucan was unchanged despite the detergent exposures.

Further, the β-1,3-glucan layer can be selectively digested using laminarinase. This was done to examine effect of different gluconases in assessing further the specificity of the carbohydrate layer on the bead. A specific β-1,3-gluconohydrolase, laminarinase, was used (FIG. 3B) and compared with the control protease, proteinase K (FIG. 3C). Laminarinase hydrolyses oligomers of glucose from glucan chains. Steadman et al., 144 J. Immunol. 2712 (1990). β-1,3-glucan beads were mixed with two concentrations of laminarinase; 0.5 U/mL and 0.1 U/mL, or in sodium acetate buffer as a control. By analysis with flow cytometry, both concentrations of laminarinase removed the β-glucan layer, evidenced by their peaks close to that of beads incubated with isotype control antibody. In contrast, when exposed to proteinase K, the β-1,3-glucan coat remained intact on the bead surface, as shown in flow cytometry (FIG. 3C). Proteinase K is a broad-spectrum serine protease and was used at two concentrations, 127 U/mL and 25 U/mL. Neither concentration showed alteration of the β-1,3-glucan layer as measured by flow cytometry using β-1,3-glucan antibody. This observation is consistent with immobilization of β-1,3-glucan through the saccharide hydroxyl groups and not through any protein contaminant present in the cell wall preparation.

Figure 4:
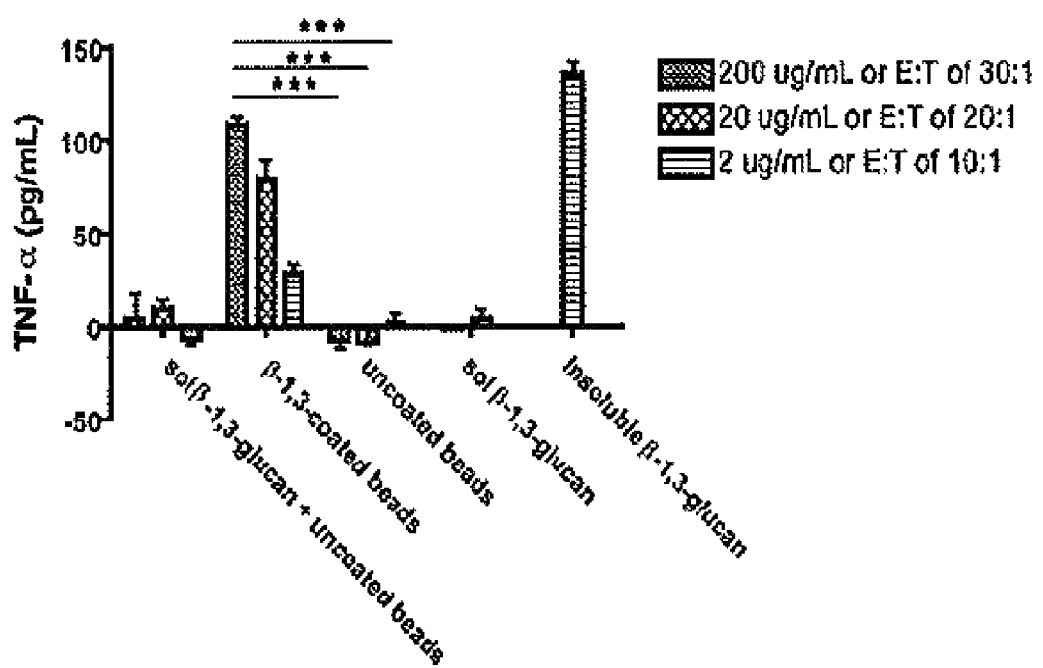
FIG. 4 demonstrates that β-1,3-glucan beads induce TNF-α secretion in a dose-dependent manner. TNF-α production was assessed by ELISA, and show that the β-1,3-glucan beads induce a higher TNF-α response in immortalized bone marrow-derived macrophages as compared to soluble β-1,3-glucan, uncoated beads, and soluble β-1,3-glucan mixed with uncoated beads. The β-1,3-glucan beads give a comparable response to the positive control, insoluble β-1,3-glucan. Data are means plus standard deviation of triplicate culture (***$p<0.001$).
Figure 7:
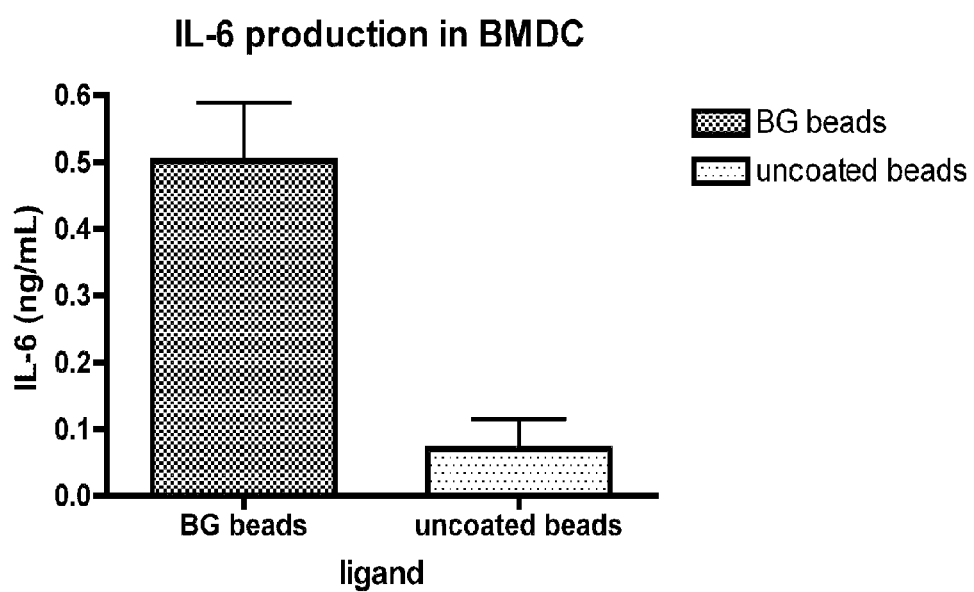
FIG. 7 is a bar graph showing the stimulation of IL-6 production in murine primary bone-marrow derived macrophages exposed to artificial fungal-like particles in a manner similar to that discussed regarding FIG. 4.

Importantly, the β-1,3-glucan beads induced TNF-α responses in a dose dependent manner. More specifically, to determine if β-1,3-glucan beads were competent to trigger an inflammatory response in professional antigen presenting cells, the β-1,3-glucan beads were incubated with immortalized bone marrow-derived macrophages (BMDM). As expected, the β-1,3-glucan-coated beads induced a higher TNF-α response compared with soluble β-1,3-glucan alone, uncoated beads, and uncoated beads mixed with β-1,3-glucan as analyzed through ELISA. Because native BMDM does not exhibit appreciable amounts of Dectin-1 expression, as determined by Western blotting, these cells were transduced with GFP-Dectin-1 in order to measure TNF-α response. The soluble β-1,3-glucan used to stimulate the BMDM was the same carbohydrate used to create the β-1,3-glucan beads. After 24 hours of stimulation of the BMDM with the aforementioned ligands, the β-1,3-glucan beads showed a significantly higher TNF-α response compared with soluble β-1,3-glucan mixed with uncoated beads, uncoated beads, or soluble β-1,3-glucan alone (FIG. 4). These results indicate that the carbohydrate must be bound to the surface of a particle in order to induce a TNF-α response. In addition, as the effector to target ration (E:T) is increased, the TNF-α response increased accordingly. The TNF-α response of the β-1,3-glucan beads is also comparable to stimulation of BMDM with 2 μg/mL of insoluble β-1,3-glucan. These artificial fungal particles also stimulated a IL-6 response (FIG. 7) in mouse primary bone-marrow derived macrophages.

Figures 5A, 5B, 5C, 5D, 5E, 5F, 5G, 5H:
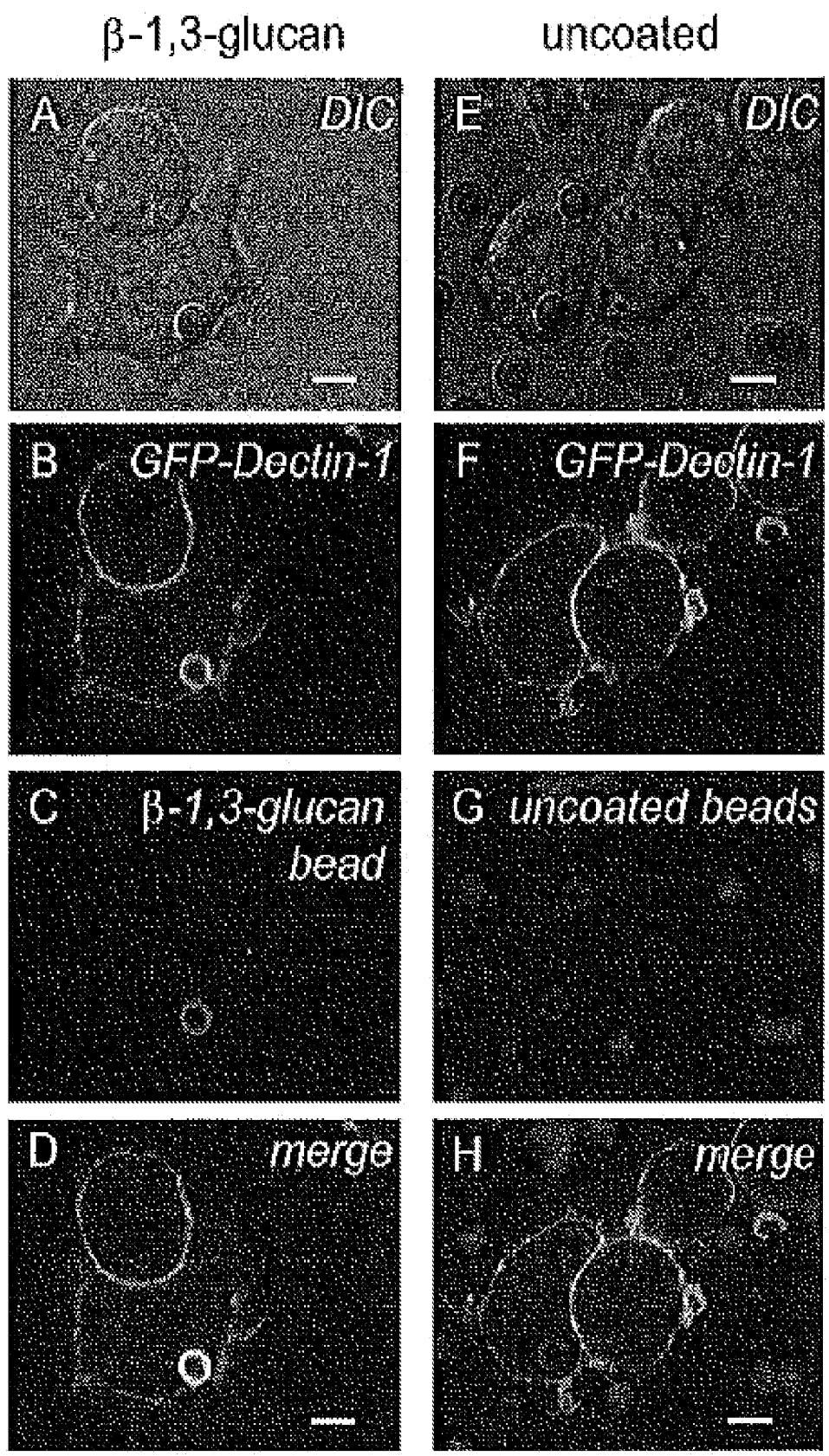
FIGS. 5A-5H show Dectin-1 recruitment to β-1,3-glucan beads in live macrophages. β-1,3-glucan beads, left column, ingested by GFP-Dectin-1 expressing RAW macrophages as compared to unconjugated beads, right column. Incubation time was 30 minutes at 37° C. Bar indicates 5 μm.
Figure 9:
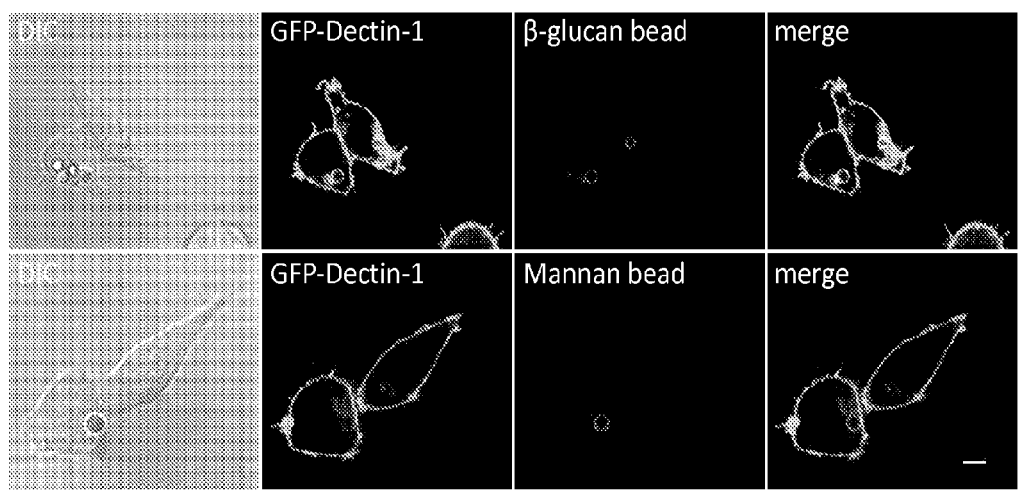
FIG. 9 presents photographs of the interaction of β-glucan and mannan conjugated beads with macrophages. Each type of bead was labeled with AF-647 for visualization and incubated with GFP-Dectin-1 RAW cells for 30 minutes. Confocal microscopy was used to capture images of the ingested beads. Images reveal that both bead types of artificial fungal pathogens were phagocytosed, but only β-glucan beads show intracellular recruitment of Dectin-1 which is the dominant receptor for β-glucan, not mannan. Bar indicates 5 μm.

Moreover, Dectin-1 is specifically recruited to phagosomes containing β-1,3-glucan beads. Dectin-1 is the major β-1,3-glucan receptor expressed on the surface of immune cells including macrophages and dendritic cells. Brown & Gordon, 413 Nat. 36 (2001). The immunological response of RAW 264.7 (RAW) macrophages expressing GFP-Dectin-1 was probed using the β-1,3-glucan coupled beads and compared with the response of uncoated polystyrene beads. When the β-1,3-glucan-coated beads are phagocytosed by the RAW macrophages (DIC, FIG. 5A), the GFP-Dectin-1 on the cell membrane is immediately recruited to the phagosome (FIG. 5B). The fluorescent signal from GFP-Dectin-1 and the P-1,3-glucan coated bead (FIG. 5C) co-localize in the merged image (FIG. 5D). In comparison, when RAW cells expressing GFP-Dectin-1 ingest uncoated polystyrene beads (FIG. 5E-5H), there is no GFP-Dectin-1 recruitment to the phagosome (FIGS. 5F, 5H), indicating the Dectin-1 recruitment is specific to β-1,3-glucan and not the bead scaffold. In a similar experiment, mannan-coated beads were phagocytosed by macrophages, but without Dectin-1 recruitment (FIG. 9).

The design of fungal like particles that maintain accurate architecture as a yeast cells, and have been endowed with purified carbohydrate surface through covalent bonding, is described herein. Biologically, these particles are recognized by the innate immune system in a similar fashion as live yeast cells; mainly through receptors that bind to carbohydrate antigens such as β-1,3-glucan. β-1,3-glucan is a major component of the outer wall of many fungi including *C. albicans*, *Aspergillus* species, *P. carinii* (agent causing PCP pneumonia), and many dimorphic agents (*Histoplasma, Coccidiodes*). Data supporting the importance of the innate immune system's ability to recognize β-1,3-glucan has been described: when individuals or families with polymorphisms in Dectin-1, the β-1,3-glucan receptor have been shown to suffer from recurrent candidal infections, implicating this receptor as a focus of antifungal immunity. Ferwerda et al., 361 N. Engl. J. Med. 1760 (2009).

The immune response of the cells contacted with the artificial fungal particles of the present invention can be assayed in known formats, including known techniques such as Western blot analysis, radioimmunoassay (RIA), Immunoradiometric assay (IRMA), chemiluminescent immunoassays, such as enzyme-linked immunosorbent assay (ELISA), multiplex bead assays, a fluorescence antibody method, passive haemagglutination, mass spectrometry (such as MALDI/TOF (time-of-flight), SELDI/TOF), liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectroscopy, and HPLC-tandem mass spectrometry (HPLC-MS/MS). Some of the immunoassays can be easily automated by the use of appropriate instruments such as the Siemens Bayer ACS 180™ Chemistry Analyzer (available widely, e.g., from Block Scientific., Inc., Bohemia, N.Y.) for a chemiluminescent immunoassay.

RIA and ELISA provide the benefit of detection sensitivity, rapidity, accuracy, possible automation of procedures, and the like, for the determination of the concentration or level of a biomarker indicative of immune response following contact with the artificial fungal particles described herein. See generally, Kazi et al., 13 J. Coll. Physicians Surg. Pak 22 (2003); Ohkuni et al., 1289 Intl. Cong. Ser. 71 (2006); Mitchell et al., 5 Mol. Microbiol. 1883 (1991); Kashyap et al., 60 J. Clin. Invest. 171 (1977). Antibody arrays or protein chips can also be employed. See, e.g., U.S. Patent Application Pubs. No. 2003/0013208, No. 2002/0155493, No. 2003/0017515; U.S. Pat. Nos. 6,329,209, 6,365,418. Other techniques can be used to as required to practice the methods described herein, according to a practitioner's preference, and based upon the present disclosure.

The immune response to the fungal like particles described herein can be further characterized in vivo using known animal models available for the study of disseminated and invasive fungal infection. For example, fungal like particles can be administered via several routes, including intramuscular, intra peritoneal and intravenous injection. The immune response is then measured at the innate level (e.g., cytokines), and adaptive (T-cell response via flow cytometry, immunoglobulin subsets), and the response compared with *C. albicans* infection.

As noted, the carbohydrate-bead conjugates of the present invention were amenable to NHS ester dye labeling. Other detectable markers suitable for labeling the present artificial fungus-lake particles include radioactive label, fluorescent label, chemiluminescent label, chromophoric label, ligand, fluorescein, phosphatase, biotin, biotin-related compounds, avidin, avidin-related compounds, peroxidase, luciferase, GFP, DS-Red, labeled antibody, etc., as such labels are well-known in the art.

Immune parameter perturbation under the effect of immunomodulatory agents can also be studied in vivo. For example, immunomodulatory agents (small molecules or biologics) can be used to pre-treat subjects, such as animal or human subjects. The response to the fungal like particles is then assessed before and after challenge with *C. albicans* or *A. fumigatus*, either in vivo in animal models or in vitro with cells, e.g., PBMCs, obtained from a human subject. Additionally, the immune response to the fungal like particles as described herein can be characterized in human subjects undergoing immunomodulatory therapy (with biologics or chemotherapeutics). Such responses can be characterized subsequently to monitor any changes in immuncompetence, such as increased evidence of immunity or resistance to fungal infection.

Additionally, the fungal like particle platform can be adapted to a biodegradable polymer that is safe for human use, which a well-known in the art (e.g., polyethylene glycol, agarose, PLGA, silk fibroin, serum albumin). Clinical lots are quality controlled through a variety of metrics including analyzing the total conjugated carbohydrate content on the bead surface and the stringency of conjugation as determined by flow cytometry, confocal- and electron-microscopy. Subjects who are being considered for biologic therapy (e.g., anti-TNF-α or Rituximab) can be identified from rheumatology, oncology, or gastrointestinal clinics. Blood will be obtained for cytokine analysis, immunoglobulins quantitation and characterization, and blood-cell isolation for flow cytometry.

Figure 6:
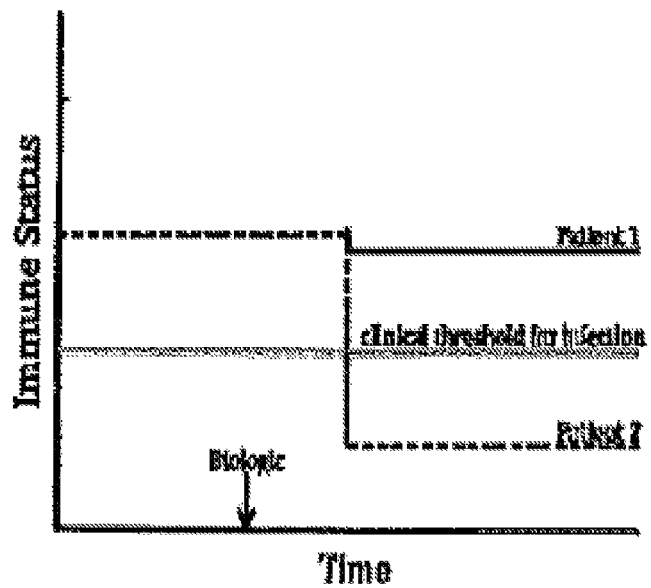
FIG. 6 reflects a simulation of two patients who undergo treatment with biologics. Patient 2 suffers a drop in anti-fungal immunity leaving high risk for infection. Patient 1 remains above the clinical threshold.

The present invention provides for the application of the platform to probe the immune response of each individual patient in preparation for immunomodulatory therapy. In this way, a patient-specific (personalized) immune "setpoint" is determined, and a true risk for subsequent invasive fungal infection may be assessed (FIG. 6). This knowledge allows healthcare providers to better design regimens for prophylactic medications, surveillance protocols, or to choose more appropriate therapeutic regimens. The prognostic methods of the invention also are useful for determining a proper course of treatment for a subject having immunodeficiency against fungal infection. A course of treatment refers, for example, to therapeutic measures taken for a patient after diagnosis or after treatment for immunoincompetence, including immunomodulatory therapy. For example, if PBMCs collected from a subject exhibit poorer immune response after contact with the artificial fungus-like particle, the physician can treat the subject with a sufficient prophylactic antifungal medication. The assessment of anti-fungal immunity can be performed on a routine basis, for example every 3 to 4 months, to monitor any evidence of declining immune reserve. If a subject falls into a "susceptible" range, modifications to a the fungal prophylatic regimen, or immunosuppressive therapeutic strategy can be made.

Example antifungal medications include polyene antimycotics (e.g., amphtercin B, candicidin, filipin, hamycin, natamycin, nystatin, rimocidin); imidazoles (e.g., bifonazole, butoconazole, clotrimazole, econazole, fenticonazole, isoconazole, ketoconazole, miconazole, omoconazole, sertaconazole, sulconazole, tiocoazole); triazoles (e.g., albaconazole, fluconazole, isavuconazole, itraconazole, posaconazole, terconazole, voriconazole; thiazoles (e.g., abafungin); allylamines (e.g., amorolfin, butenfine, naftifine, terbinafine), echinocandins (e.g. anidulafungin, caspofungin, micafungin); benzoic acid; ciclopirox olamine; flucytosine or 5-fluorocytosine; griseofulvin; haloprogin; tolnaftate; undecylenic acid; or triarylmethane dye. Alternatively, the subject may be vaccinated and allowed to develop at least some immunity to fungal infection before further immunomodulatory therapy is initiated.

On the other hand, if an individual's setpoint shows robust reserve, making the likelihood of future infection unlikely, the physician-patient team may feel more comfortable pressing ahead with immunomodulatory therapy, with the knowledge that the patient may likely have a successful outcome free of invasive fungal infection. Example immunomodulatory medicines (immunosuppressive agents) that may be used to treat the subject include calcineurin inhibitors (e.g., cyclosporine, tacrolimus, sirolimus); antiproliferative drugs (e.g., taxane, cisplatin, azathioprine, clyclophosphamide, methotrexate, chloambucil, mycophenolate mofetil, mercaptopurine, and other known anti-cancer therapeutic agents); glucocorticosteroids (e.g., prednisolone); or antibodies (e.g., muromonab CD3, antithymocyte clobin, Rho (D) immuneglobin, efalizumab, basiliximab, daclizumab); interferons (e.g., IFN-β, IFN-γ); TNF-α binding proteins (e.g., infliximab, etanercept, adalimumab); mycophenolic acid; fingolimod; or myriocin.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of a disease. The methods of the invention contemplate any one or more of these aspects of treatment.

The term "effective amount" used herein in the context of treatment refers to an amount of a compound or composition sufficient to assess the immunocompetency of the subject; or to treat a specified disorder, condition or disease such as ameliorate, palliate, lessen, and/or delay one or more of its symptoms. In the context of determining the immunocompetency of a subject population of cell or the immunocompetency of a subject, effective amount refers to amount sufficient to obtain these goals.

The term "subject" or "individual" refers to a mammal and includes human, bovine, horse, feline, canine, rodent, or primate. In some embodiments, the subject is human. In some embodiments, the artificial fungal particles of the present invention are suitable for in vivo delivery As used herein, the term "in vivo delivery" refers to delivery of the fungus-like particles to the subject by such routes of administration as oral, intravenous, subcutaneous, intraperitoneal, intrathecal, intranasal, intramuscular, inhalational, topical, transdermal, rectal (suppositories), vaginal, and the like.

The present invention is also directed to commercial kits for the evaluation of a subject's or a subject's cells' immune reaction in response to exposure to the artificial fungal particle of the present invention. The kit can be in any configuration as known to those of skill in the art and is useful for performing one or more of the methods described herein for the quantitation of at least one biomarker or cellular activity indicative of immune response to the artificial fungal particle. For example, the kit may include β-1,3-glucan-conjugated polymer beads. The kits can supply many, if not all, essential reagents for conducting an assay for the detection of an immune response of cell in a test biological sample (e.g., a blood, PBMC, or marrow sample), such as described (e.g., an ELISA for analyzing TFF-α response). The kit may also include appropriate standards or controls. The kit may be used in conjunction with known computer readable systems and automated assays.

In summary, the present embodiments provide for compositions and convenient methods to prepare carbohydrate- (e.g., β-1,3-glucan-) coated particles that serve as "artificial fungal pathogens" and elicit a specific anti-fungal (e.g., an anti-Dectin-1) response in mammalian immune cells. For example, β-1,3-glucan-beads engaged Dectin-1, as shown by confocal fluorescence microscopy and inflammatory cytokine responses, specifically TNF-α response, in bone marrow-derived macrophages. This system allowed specific analysis of TNF-α to a pure β-1,3-glucan fraction, as opposed to using cell wall particulates, which contain multiple cell wall carbohydrates and other protein components, generating non-specific responses to Dectin-1. Due to the stability and purity of the β-1,3-glucan surface, these beads are useful for immunoprecipitation studies to purify receptors and other proteins associated with this fungal-derived carbohydrate. Additional available amine sites on the bead surface also permit the incorporation of labels (e.g., fluorescent labels) to track beads during cell interactions. These additional conjugation handles allow incorporation of other relevant pathogen-derived molecules to dissect the specific contribution of these ligands in the immune response. Thus, these beads provide for multifunctional adjuvants or immunotherapeutic agents for modulating immune responses.

The invention can be further illustrated by any of the following numbered paragraphs.

1. An assay for determining whether a population of cells is immunocompromised for fungal infection comprising: obtaining a population of cells; contacting the cells with an artificial fungus-like particle comprising a purified fungal cell wall carbohydrate conjugated to a polymer bead; observing the response of the cells to the particle; and comparing the response with a known response of a healthy, immunocompetent cell population.

2. The assay of paragraph 1, wherein the purified fungal cell wall carbohydrate is β-glucan, mannan, or β-1,3-glucan.

3. The assay of paragraph 1, wherein the polymer bead is 3 μm±35% in size.

4. The assay of any one of the preceding paragraphs, wherein the carbohydrate is conjugated by covalent bonds to the polymer bead.

5. The assay of any one of the preceding paragraphs, further comprising a label.

6. The assay of any one of the preceding paragraphs, further comprising a fungal pathogen-derived component.

7. The assay of paragraph 6, wherein the pathogen-derived component is a fungal cell-wall component.

8. The assay of any one of the preceding paragraphs, wherein the particles represent a monodisperse population of artificial pathogens that replicate the size and geometry of pathogenic yeast.

9. The assay of any one of the preceding paragraphs, wherein the polymer is biodegradable.

10. The assay of any one of paragraphs 1-8, wherein the polymer is polystyrene.

11. The method of paragraph 1, wherein contacting is for a period of 8 to 24 hours±1%.

12. The assay of paragraph 1, wherein the purified fungal cell-wall carbohydrate is β-1,3-glucan and the response is binding of β-1,3-glucan to Dectin-1 on the cell surface.

13. The assay of paragraph 1, wherein the response is a cytokine response.

14. The assay of paragraph 13, wherein the cytokine response is a TNF-α or IL-6 response.

15. The assay of paragraph 1, wherein the response is phagocytosis.

16. The assay of paragraph 1, wherein the population of cells comprises peripheral blood mononuclear cells or bone marrow cells.

17. The assay of paragraph 1, wherein the population of cells is obtained from a human subject.

18. The assay of claim 1, wherein the observing is achieved by immunoassay, FACS, or microscopy.

19. The assay of any of the preceding paragraphs, wherein the assay is an automated assay.

20. A composition comprising a monodisperse population of artificial pathogens that mimic the size and shape of pathogenic yeast, comprising a purified fungal cell-wall component conjugated to a polymer bead.

21. The composition of paragraph 20, wherein the purified fungal cell-wall component is a carbohydrate.

22. The composition of paragraph 21, wherein the purified carbohydrate is β-glucan, mannan, or β-1,3-glucan.

23. The composition of any one of paragraphs 20-22, wherein the polymer bead is 3 μm±35% in size.

24. The composition of any one paragraphs 20-23, wherein the polymer is polystyrene.

25. The composition of any one of paragraphs 20-23, wherein the polymer is biodegradable.

26. The composition of any one of paragraphs 20-15, wherein the carbohydrate is conjugated by covalent bonds to the polymer bead.

27. The composition of paragraph 26, wherein the conjugation is achieved by conjugation using 1,1'-carbonyldiimidazole.

28. The composition of any one of paragraphs 20-27, further comprising a label.

29. The composition of any one of paragraphs 20-28, further comprising a fungal pathogen-derived component.

30. The composition of paragraph 29, wherein the pathogen-derived component is a fungal cell wall component.

31. The use of the composition of any one of paragraphs 20-30 for immuno-precipitation studies to purify receptors and other proteins associated with the purified fungal carbohydrate.

32. The use of the composition of any one of paragraphs 20-30 to identify immunodeficiency.

33. The use of the composition of any one of paragraphs 20-30 to directly probe the immune response to β-1,3-glucan.

34. The use of a composition comprising an artificial fungus-like particle comprising β-1,3-glucan conjugated to a polymer bead to probe pathways related to Dectin-1, a receptor for β-1,3-glucan.

35. A kit comprising the composition of any one of paragraphs 20-30.

36. The kit of paragraph 35, wherein the kit is suitable for use in a diagnostic assay.

37. The kit of paragraph 36, wherein the diagnostic assay is an automated assay.

38. A method for treating a subject with immunomodulatory therapy comprising: obtaining a population of peripheral blood mononuclear cells or bone marrow cells from the subject; contacting the cells with artificial fungus-like particles comprising purified β-1,3-glucan or mannan conjugated to a polymer bead; observing the cellular response to the artificial fungus-like particles; comparing the cellular response with a known non-immunocompromised, healthy baseline response; and administering a prophylactic agent to the subject.

39. A method for treating a subject with immunomodulatory therapy comprising administering to the subject a composition comprising artificial fungus-like particles comprising purified β-1,3-glucan or purified mannan conjugated to a biodegradable polymer bead; subsequently observing the subject's immune response to the artificial fungus-like particles; comparing the cellular response with a known non-immunocompromised, healthy baseline response; and administering a prophylactic agent to the subject.

EXAMPLES

Example 1

Preparation and Analysis of β-1,3-glucan Conjugated Microspheres

A 300 μL of stock solution containing 3 μm amine-coated polystyrene beads ($1.67 \times 10^9$ beads/mL, Polysciences, Warrington, Pa.) were washed three times in dimethylsulfoxide (DMSO) (Sigma-Aldrich, St. Louis, Mo.) using centrifugal filters containing a 0.45 μm PTFE membrane (Ultrafree brand, Millipore, Billerica, Mass.). Beads were resuspended in anhydrous DMSO. The amino groups on the beads were then activated by adding 1,1'-carbonyldiimidazole (CDI, Sigma-Aldrich) at a final concentration of 0.5 M CDI in anhydrous DMSO. The bead/CDI mixture was then shaken at room temperature (RT) for 1 hr. Beads were rinsed three times in anhydrous DMSO using centrifugal filters, then resuspended in DMSO. Approximately 10 mM of β-1,3-glucan (Wellmune, Biothera, *S. cerevisiae*, Eagan, Minn.) dissolved in DMSO was added. The mixture was shaken at RT for 1 hr. The beads were filtered using centrifugal filters to remove DMSO, and resuspended in PBS. After washing thrice in PBS, the bead mixture was resuspended in PBS and stored at 4° C. Carbohydrate content on the bead surface was analyzed using the phenol-sulfuric acid assay. Dubois et al., Analyt. Chem. 350 (1956).

After carbohydrate loading, beads were also fluorescently dyed for live-cell imaging by mixing an aliquot of beads ($\sim 50 \times 10^6$) with 30 μg of N-hydroxysuccinimidyl ester activated Alexa Fluor (AF) dye (Invitrogen) for 1 hr at RT. For labeling experiments, AF405 (ex: 401/em: 421) and AF647 (ex: 650/em: 655) were used. Excess dye was removed with three washes in PBS, and the beads were used immediately in imaging experiments.

Immune-Transmission Electron Microscopy (TEM) of β-1,3-glucan Microspheres:

The primary antibody mouse-anti-β-1,3-glucan (Biosupplies, Parksville, Australia) was incubated for 1 hr at RT with an equal volume of secondary goat-anti-rabbit labeled 15 nm gold (Ted Pella, Redding, Calif.) at final concentrations of 1:10 for the anti-β-1,3-glucan and 1:30 for the secondary antibody. This antibody-gold mixture was then as pelleted and incubated with the bead samples for 1 hr at RT. Beads were pelleted again and rinsed once in 0.1 M sodium cacodylate buffer, pH 7.4 (Electron Microscopy Sciences (EMS), Hatfield, Pa.). They were then post-stained with a mixture of 0.1% ruthenium red (EMS) plus 1.0% osmium tetroxide (EMS) in eacodylate buffer for 1 hr at RT. They were pelleted again and rinsed once with buffer, then stabilized in 2.0% agarose for ease of handling. The pellets were dehydrated through a graded series of ethanol washes and embedded in Eponate resin (Ted Pella, Redding, Calif.) at 60° C. overnight. Thin sections were cut on a Leica EM UC7 and collected onto fonnvar-coated slot grids. Sections were examined in a JEOL 1011 transmission electron microscope at 80 kV and images were collected using an AMT digital imaging system (Advanced Microscopy Techniques, Danvers, Mass.).

Analysis of Microspheres by Flow Cytometry:

Approximately 50,000 beads, as determined by manual counting using a hemacytometer, were incubated in 400 μL of PBS with 2% bovine serum albumin (BSA, Sigma Aldrich) (PBS/BSA) for 1 hr at RT. After washing, 0.25 μg of anti-β-1,3-glucan antibody (monoclonal mouse IgG, Biosupplies, Parksville, Australia) or relevant isotype control (anti-AP3, mouse IgGI, Santa Cruz Biotechnology, Santa Cruz, Calif.) was added for 1 hr at RT in PBS/BSA solution and then washed thrice in PBS/BSA solution. Beads were resuspended in 400 μL of PBS/BSA and 2 μg of polyclonal rabbit anti-mouse IgG-Alexa Fluor 488 antibody (Molecular Probes, Eugene, Oreg.) was added for 1 hr at RT in the dark. After washing, beads were resuspended in 400 μL PBS/BSA and assessed for surface fluorescence on a FACS Calibur (Bectin-Dickinson, Franklin Lakes, N.J.). Flow cytometry analysis was performed using FlowJo software (Tree Star Inc., Ashland, Oreg.).

Figure 8:
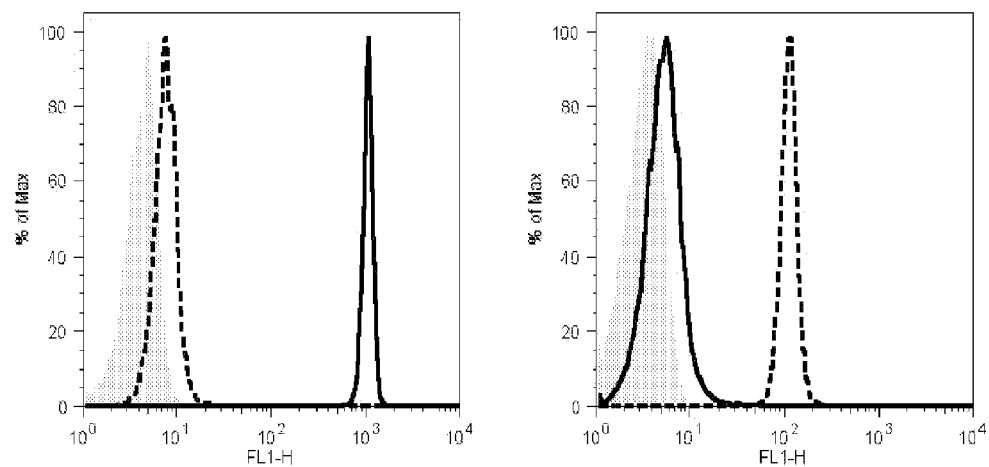
FIG. 8 shows analysis of β-glucan (left panel) and mannan beads (right panel) by flow cytometry. Using anti-β-glucan antibody and conconavalin-A (ConA), the composition of each bead type was distinguished by flow cytometry. ConA recognizes mannan residues and not β-glucan, whereas the anti-β-glucan antibody binds β-glucan and not mannan. Shaded histogram: negative control; dashed line: ConA; and solid dark line: anti-β-glucan antibody.

In another experiment, β-glucan and mannan beads were compared using flow cytometry using anti-β-1,3-glucan antibody, which does not bind mannan, and conconavalin A, which does not bind β-1,3-glucan. The ligands were able to bind with specificity to the appropriate carbohydrate-conjugate bead, as shown in FIG. 8. Conjugation of mannan is described in Example 3.

Stability of β-1,3-glucan when Exposed to Detergents:

Approximately 50,000 β-1,3-glucan microspheres were incubated with various detergent conditions oscillating for 1 hr at 4° C. SDS (1% and 0.5%) (Sigma-Aldrich), NP-40 (1%) (Sigma-Aldrich), and Brij (1% Brij 58, 10 mM Tris [pH 7.8], 150 mM NaCl, 5 mM $MgCl_2$, 0.5%) (Sigma-Aldrich) detergents were used to test the stability of the β-1,3-glucan layer on the bead surface. After washing with PBS/BSA, β-1,3-glucan microspheres were assessed for β-1,3-glucan content using immunofluoreseence by flow cytometry as described herein.

Digestion of β-1,3-glucan with Laminarinase:

Approximately 25,000 β-1,3-glucan beads were placed into 0.1 M sodium acetate buffer, pH 5.0 (Sigma-Aldrich) or PBS. Several concentrations of laminarinase (derived from *Trichoderma* species, Sigma-Aldrich) (0.1 U/mL and 0.5 U/mL) or proteinase K (Sigma-Aldrich) (25 U/mL and 127 U/mL) were added and incubated overnight at 37° C. on a rotating drum. Beads were washed with PBS/BSA solution and then analyzed for β-glucan content using the phenol-sulfuric method, confocal microscopy or immunofluorescence as described.

Example 2

In Vitro Characterization of β-1,3-glucan-Coated Microspheres

RAW 264.7 Cell Culture:

RAW 264.7 macrophage cell lines were cultured in Dulbecco's modified Eagle's medium (DMEM) containing 10% fetal bovine serum (FBS) (HyClone, ThermoScientific, Logan, Utah), 1% penicillin/streptomycin (Gibco, Invitrogen, Carlsbad, Calif.), and 1% L-glutamine (Gibco, Invitrogen). Cells were grown at 37° C. with 5% $CO_2$ for 2 days to ensure log-phase growth of the cells in order to optimize their ability to engulf particles. Two hr prior to imaging, RAW cells were re-plated into the chambered coverglass with DMEM medium containing 20% FBS, 2% penicillin/streptomycin, and 2% L-glutamine.

Lentiviral Transduction:

HEK293T cells were cultured in DMEM containing 10% FBS, 1% L-glutamine, and 1% penicillin/streptomycin as described previously (Anavanis-Tsakonas et al., 193 PNAS 15945 (2006)), and used to generate lentivirus. eGFP-Dectin-1 was subcloned into the pHAGE II vector, a fourth-generation lentiviral self-inactivating nonreplicative vector used for transduction of bone marrow stem cells. Sommer et al., 28 Stem Cells 64 (2008). Lentivirus was made as described. Anavanis-Tsakonas et al., 2006. Cellular transduction was done in 12-well plates whereby 100 μL of concentrated viral supernatant was placed onto plated cells and incubated at 37° C. overnight. Supernatants were replaced with normal media the following day, and cells were selected using 5 μg/mL puromycin. Successful infection was determined by puromycin resistance and direct examination under an epifluorescence microscope for the presence of green fluorescence.

Measuring TNF-α Production Using ELISA:

Immortalized bone marrow-derived macrophages (BMDM) from BL6 mice were transduced with GFP-Dectin-1 lentivirus and plated in a 96-well plate at $5×10^4$ cells/well. Cells were stimulated with the following ligands and corresponding concentrations or effector to target cell ratios (E:T): soluble β-1,3-glucan (2 μg/mL, 20 μg/mL, 200 μg/mL), β-1,3-glucan beads (E:T of 10:1, 20:1, and 30:1), uncoated beads (E:T of 10:1, 20:1, and 30:1), soluble β-1,3-glucan mixed with uncoated beads (2 μg/mL, 20 μg/mL, 200 μg/mL—each concentration mixed with uncoated beads at an E:T of 20:1). Insoluble β-1,3-glucan (2 μg/mL) was also used as a positive control. BMDM were stimulated for 24 hr, and fresh supernatents were analyzed using an ELISA assay measuring TNF-α (DuoSet, Dy410) developed by R&D Systems (Minneapolis, Minn.). Statistical analysis was done in GraphPad Prism4 using Two-Way ANOVA with Bonferroni post tests.

Assay for IL-6 Stimulation:

Primary bone-marrow derived dendritic cells (BMDC's) were isolated from 4-12 week old C57BL/6 mice (Jackson Laboratories, Bar Harbor, Me.) according the a previously published protocol. Lutz et. al, 223 J. Immunol. Meth. 77 (1999). On day 5 of culture, cells were plated in a 96 well plate at a density of $1×10^6$ cells/well. On day 6, the cells were stimulated with β-1,3-glucan beads and uncoated beads at a E:T ratio of 25:1. BMDC were stimulated for 24 hr, and fresh supernatents were analyzed using an ELISA assay measuring IL-6 (DuoSet, DY406) developed by R&D Systems (Minneapolis, Minn.). Statistical analysis was done in GraphPad Prism4 using Two-Way ANOVA with Bonferroni post tests.

Confocal Microscopy:

GFP-Dectin-1 RAW cells, or β-1,3-glucan microspheres immunostained with anti-β-1,3-glucan antibody were plated onto confocal dishes (LabTek, ThermoScientific, Rochester, N.Y.). Cells were incubated with AF647 dyed-β-1,3-glucan microspheres for 30 min at 37° C.×5% $CO_2$ in complete media (DMEM supplemented with 10% FBS, penicillin, streptomycin, and L-glutamine). After washing, slides were mounted onto a Nikon Ti-B inverted microscope fitted with a spinning disc confocal detection head (Yokogawa, Sugar Land, Tex.). A 4 W, continuous-wave laser (Coherent, Santa Clara, Calif.) or solid-state UV laser were used to produce excitation wavelengths of 405 nm or 647 nm. Cells and beads were imaged using a Nikon 100× objective with high numerical aperture (Nikon, 1.49 NA, oil immersion). Images were captured using an EM-CCD camera (Hamamatsu, C9100-13, Bridgewater, N.J.) and analyzed using Metamorph software (Molecular Devices, Downington, Pa.). Tam et al., 5 PLoS ONE e15215 (2010).

Example 3

Preparation of Mannan-Conjugated Artificial Fungal Particles

A 300 μL of stock solution containing 3 μm amine-coated polystyrene beads ($1.67×10^9$ beads/mL, Polysciences, Warrington, Pa.) were washed three times in dimethylsulfoxide (DMSO) (Sigma-Aldrich) using centrifugal filters containing a 0.45 μm PTFE membrane (Ultrafree brand, Millipore, Billerica, Mass.). Beads were resuspended in anhydrous DMSO. The amino groups on the beads were then activated by adding 1,1'-carbonyldiimidazole (CDI, Sigma-Aldrich) at a final concentration of 0.5 M CDI in anhydrous DMSO. The bead/CDI mixture was then shaken at RT for 1.5 hr. Beads were rinsed three times in anhydrous DMSO using centrifugal filters, then resuspended in DMSO. Approximately 5 mM-10 mM of mannan from *S. cerevisiae* (Sigma-Aldrich) dissolved in DMSO was added. The mixture was shaken at RT for 1.5 hr. The beads were filtered using centrifugal filters to remove DMSO, and resuspended in PBS. After washing thrice in PBS, the bead mixture was resuspended in PBS and stored at 4° C. Carbohydrate content on the bead surface was analyzed using the phenol-sulfuric acid assay. Dubois et al., 26 Anal. Chem. 350 (1956).

Flow cytometry characterization of the mannan conjugated artificial fungal particle, compared with β-1,3-glucan conjugated particles, is discussed in Example 1. Additionally, beads were labeled with AF-647 and interacted with macrophages as described above. Phagocytosis was visualized (FIG. 9).

The invention claimed is:

1. An assay for determining whether a population of cells is immunocompromised for fungal infection comprising:
   obtaining a population of cells;
   contacting the cells with an artificial fungus-like particle comprising a purified fungal cell wall carbohydrate conjugated to a polymer bead;
   observing the response of the cells to the particle; and
   comparing the response with a known response of a healthy, immunocompetent cell population.

2. The assay of claim 1, wherein the purified fungal cell wall carbohydrate is β-glucan, mannan, or β-1,3-glucan.

3. The assay of claim 1, wherein the carbohydrate is conjugated by covalent bonds to the polymer bead.

4. The assay of claim 1, further comprising a label.

5. The assay of claim 1, further comprising a fungal pathogen-derived component.

6. The assay of claim 5, wherein the pathogen-derived component is a fungal cell-wall component.

7. The assay of claim 1, wherein the particles represent a monodisperse population of artificial pathogens that replicate the size and geometry of pathogenic yeast.

8. The assay of claim 1, wherein the polymer is biodegradable.

9. The assay of claim 1, wherein the polymer is polystyrene.

10. The method of claim 1, wherein contacting is for a period of 8 to 24 hours±1%.

11. The assay of claim 1, wherein the purified fungal cell-wall carbohydrate is β-1,3-glucan and the response is binding of β-1,3-glucan to Dectin-1 on the cell surface.

12. The assay of claim 1, wherein the response is a cytokine response.

13. The assay of claim 12, wherein the cytokine response is a TNF-α or IL-6 response.

14. The assay of claim 1, wherein the response is phagocytosis.

15. The assay of claim 1, wherein the population of cells comprises peripheral blood mononuclear cells or bone marrow cells.

16. The assay of claim 1, wherein the population of cells is obtained from a human subject.

17. The assay of claim 1, wherein the observing is achieved by immunoassay, FACS, or microscopy.

18. The assay of claim 1, wherein the assay is an automated assay.

* * * * *